(12) United States Patent
Sweeting et al.

(10) Patent No.: US 12,123,775 B2
(45) Date of Patent: Oct. 22, 2024

(54) METHOD AND APPARATUS FOR THE DETECTION OF EXPOSURE TO ULTRAVIOLET LIGHT

(71) Applicant: 15814057 CANADA INC., Oakville (CA)

(72) Inventors: Chad Mitchell Sweeting, Penetanguishene (CA); Andrew Bradley Martinko, Oakville (CA); Derek Matti Harry Jouppi, Kitchener (CA); Tim Wu, Waterloo (CA); Kevin Quang Vinh Dang, Guelph (CA); Cameron Spencer Mills, Belleville (CA); Sabrina Chwen-Huei Chang, Kitchener (CA); Charles Andrew Goertz, Kitchener (CA); Colin Ellison Pierce, Waterloo (CA); Chelsea Leung, Scarborough (CA); Sanjay Manhas, Toronto (CA)

(73) Assignee: 15814057 CANADA INC., Oakville, CA (US)

( * ) Notice: Subject to any disclaimer, the term of this patent is extended or adjusted under 35 U.S.C. 154(b) by 1280 days.

(21) Appl. No.: 16/612,309

(22) PCT Filed: May 10, 2018

(86) PCT No.: PCT/IB2018/053269
§ 371 (c)(1),
(2) Date: Nov. 8, 2019

(87) PCT Pub. No.: WO2018/207133
PCT Pub. Date: Nov. 15, 2018

(65) Prior Publication Data
US 2020/0191649 A1 Jun. 18, 2020

Related U.S. Application Data

(60) Provisional application No. 62/504,742, filed on May 11, 2017.

(51) Int. Cl.
*G01J 1/50* (2006.01)
*C07K 14/78* (2006.01)
*C09K 9/02* (2006.01)

(52) U.S. Cl.
CPC ............... *G01J 1/50* (2013.01); *C07K 14/78* (2013.01); *C09K 9/02* (2013.01); *C09K 2211/1007* (2013.01); *C09K 2211/1018* (2013.01)

(58) Field of Classification Search
CPC ........................................................ G01J 1/50
See application file for complete search history.

(56) References Cited

U.S. PATENT DOCUMENTS 4,705,046 A 11/1987 Robillard
4,829,187 A 5/1989 Tomita et al.
(Continued)

FOREIGN PATENT DOCUMENTS

JP H09061235 A 3/1997
JP H10272930 A 10/1998
(Continued)

OTHER PUBLICATIONS

USPTO, Notice of Allowance and Fee(s) Due, Aug. 14, 2019, re U.S. Appl. No. 16/074,818.
(Continued)

*Primary Examiner* — David P Porta
*Assistant Examiner* — Carolyn Fin
(74) *Attorney, Agent, or Firm* — Renner, Otto, Boisselle & Sklar, LLP (57) ABSTRACT

A device for detecting exposure to light includes: a photo-responsive layer including a photochromic material; a skin-mimicking cover layer covering a first side of the photo-
(Continued)

responsive layer; and an adhesive layer configured to couple a second side of the photo-responsive layer opposite the first side to a surface.

19 Claims, 9 Drawing Sheets

(56) References Cited

U.S. PATENT DOCUMENTS

| | | | |
|---|---|---|---|
| 5,028,792 | A | 7/1991 | Mullis |
| 5,387,798 | A | 2/1995 | Funakoshi et al. |
| 5,581,090 | A | 12/1996 | Goudjil |
| 5,986,273 | A | 11/1999 | Tripp et al. |
| 6,046,455 | A | 4/2000 | Ribi et al. |
| 6,130,435 | A | 10/2000 | Rocklin |
| 6,465,791 | B1 | 10/2002 | Ribi et al. |
| 6,818,904 | B1 | 11/2004 | Ferren et al. |
| 7,101,497 | B2 | 9/2006 | Tanaka et al. |
| 9,658,101 | B1 | 5/2017 | Levine et al. |
| 2002/0117633 | A1 | 8/2002 | Questel et al. |
| 2004/0178394 | A1 | 9/2004 | Tanaka et al. |
| 2005/0067580 | A1 | 3/2005 | Fontaine |
| 2006/0001895 | A1 | 1/2006 | Yatomi |
| 2007/0269496 | A1* | 11/2007 | Gamble ............... A61P 17/16 424/59 |
| 2008/0185534 | A1 | 8/2008 | Simon et al. |
| 2008/0259315 | A1 | 10/2008 | Mersch |
| 2009/0098521 | A1* | 4/2009 | Kuo ................. G09B 23/30 434/267 |
| 2010/0163749 | A1* | 7/2010 | Hunwick, III ......... G01K 11/12 250/474.1 |
| 2010/0198177 | A1 | 8/2010 | Yahiaoui et al. |
| 2014/0038305 | A1 | 2/2014 | Sharavara et al. |

FOREIGN PATENT DOCUMENTS

| | | |
|---|---|---|
| JP | H10300576 A | 11/1998 |
| JP | 2002310785 A | 10/2002 |
| JP | 2005264155 A | 9/2005 |
| WO | WO-0203949 A2 | 1/2002 |
| WO | WO-2005067580 A2 | 7/2005 |
| WO | 2008144541 A1 | 11/2008 |
| WO | WO-2015115329 A1 | 8/2015 |
| WO | WO-2017134583 A1 | 8/2017 |

OTHER PUBLICATIONS

EPO, Extended European Search Report, Aug. 28, 2019, re European Patent Application No. 17747082.0.

International Search Report dated Apr. 25, 2017 for PCT Internatioan Application No. PCT/IB2017/050547.

Written Opinion of the International Searching Authority dated Apr. 25, 2017 for PCT International Application No. PCT/IB2017/050547.

WIPO/IB, International Preliminary Report on Patentability, Aug. 7, 2018, re PCT International Patent Application No. PCT/IB2017/050547.

ISA/CA, International Search Report and Written Opinion, Aug. 3, 2018, re PCT International Patent Application No. PCT/IB2018/053269.

USPTO, Non-Final Rejection, Mar. 7, 2019, re U.S. Appl. No. 16/074,618.

ISA/CA, International Preliminary Report on Patentability Nov. 21, 2019, re PCT International Patent Application No. PCT/IB2018/053269.

U.S. Appl. No. 16/074,618, Method and Apparatus for the Detection of Exposure to Ultraviolet Light, filed Aug. 1, 2018.

* cited by examiner

METHOD AND APPARATUS FOR THE DETECTION OF EXPOSURE TO ULTRAVIOLET LIGHT

CROSS-REFERENCE TO RELATED APPLICATIONS

This application claims priority from U.S. provisional patent application No. 62/504,742 filed May 11, 2017, the entirety of which is incorporated herein by reference.

FIELD

The specification relates generally to detecting when surfaces are exposed to light, and specifically to a method and apparatus for the detection of exposure to ultraviolet light.

BACKGROUND

Ultraviolet (UV) light—light with a wavelength of approximately 10 nm to 400 nm—is emitted by the sun at all times. UV light can have a positive effect upon human health (e.g. by inducing the production of vitamin D), but excessive exposure can be dangerous. Overexposure to UV light can cause skin damage, resulting in sunburns and an increased risk of skin cancer. Consequently, skin protection products which block UV light, such as sunscreen creams, sprays, gels and the like, are often employed to protect the skin from prolonged exposure to the sun. Sunscreen products may be used in an inexact manner, however. Once applied, it may not be known when the sunscreen is no longer providing protection against UV light. Other solutions to determining whether the sunscreen is providing UV protection include estimating the duration provided by the manufacturer of the sunscreen found on the bottle, or systems that exist to warn users of their exposure through a time based method. Such solutions may be prone to inaccuracy, however, since sunscreen may wear off differently based on what activities or environment a user is in. As a result, it may not be apparent to the user that they are exposed and at risk of getting a sunburn. Different activities done outside, as well as different skin types, result in sunscreen wearing off of a user's skin at different rates, with the attendant possible deleterious effects of overexposure.

SUMMARY

According to an aspect of the specification, a device for detecting exposure to light is provided, including: a photo-responsive layer including a photochromic material; a skin-mimicking cover layer covering a first side of the photo-responsive layer; and an adhesive layer configured to couple a second side of the photo-responsive layer opposite the first side to a surface.

BRIEF DESCRIPTIONS OF THE DRAWINGS

Embodiments are described with reference to the following figures, in which.

DETAILED DESCRIPTION OF THE EMBODIMENTS

Figure 1A:
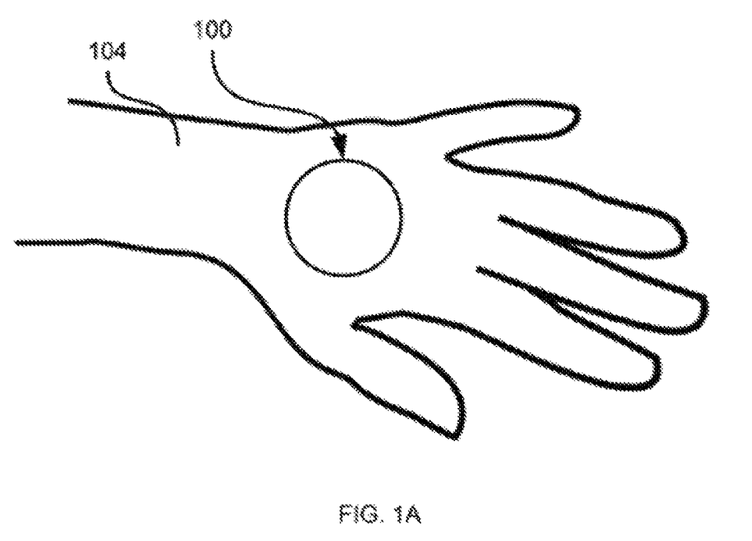
FIGS. 1 and 2 depict a device for detecting exposure to light in first and second visual appearances, according to a non-limiting embodiment.
Figure 1B:
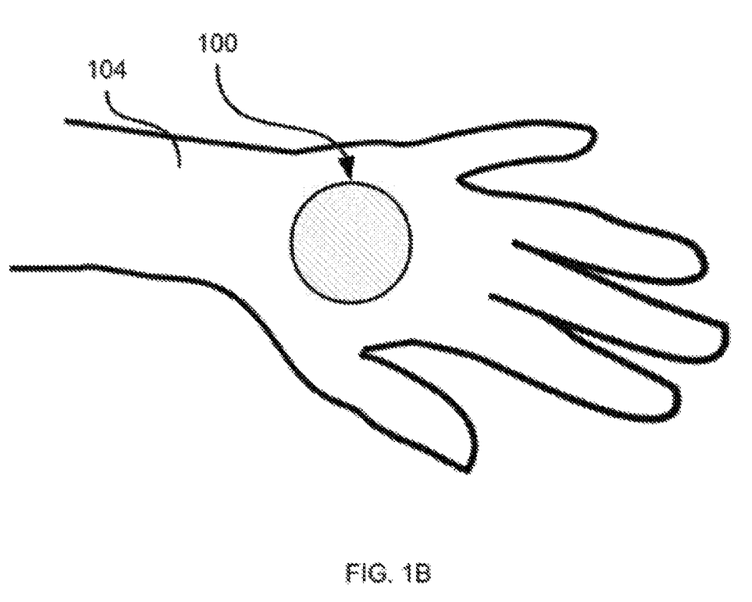

FIGS. 1A and 1B depict a device 100 for detecting exposure to light according to certain embodiments. More specifically, the device 100 is configured for attachment to a surface in order to detect exposure of the surface to light. In the example illustrated in FIGS. 1A and 1B, the device 100 is applied to the skin 104 of a human user in order to detect and indicate whether the skin 104 is exposed to light. In some embodiments, the device 100 detects and indicates whether the surface (e.g. the skin 104) is exposed to ultraviolet light having a wavelength of about 10 nm to about 400 nm, whether the surface is exposed to other wavelengths of light or not.

As will be apparent throughout the discussion herein, although the device 100 and variations thereof are described as being applied to human skin for detecting and indicating exposure to ultraviolet light, in other embodiments the device is applied to other surfaces. In further embodiments, the device is configured to detect and indicate other wavelengths of electromagnetic radiation than ultraviolet light.

As will be discussed below in greater detail, the device 100 includes a photo-responsive layer configured to have a first visual appearance in the presence of light of a predetermined wavelength. The photo-responsive layer is also configured to have a second visual appearance in the absence of the above-mentioned light. The term "visual appearance" as used herein refers to the appearance of the device 100 to human vision.

The photo-responsive layer is further configured to reversibly transition between the first and second visual appearances in response to the presence or absence, respectively, of the predetermined wavelength of light. As will be apparent to those skilled in the art, the terms "presence" and "absence" are used herein for illustrative purposes, but do not define absolute requirements. Thus, in some embodiments the device 100 transitions to the second visual appearance when light of the predetermined wavelength (e.g. ultraviolet) is present at sufficiently low levels, rather than entirely absent.

The device 100 is employed, in certain embodiments, to detect and indicate when the skin 104 of the user is exposed to ultraviolet light due to the absence of sunscreen (e.g. because no sunscreen has been applied, or because previously applied sunscreen has worn off, been chemically inactivated, or the like). FIG. 1A, for example, illustrates the device 100 in the absence of ultraviolet light (i.e. in the second visual appearance as mentioned above), due to the presence of sunscreen on the device 100 and surrounding skin 104. In the second visual appearance as shown in FIG. 1A, the device 100 is substantially colourless and transparent in the illustrated embodiment.

When the sunscreen has worn off (e.g. due to contact with water or other fluids such as sweat, physical abrasion or the like) or otherwise been rendered ineffective at absorbing ultraviolet radiation, the device 100, being exposed to the ultraviolet radiation, transitions to the first visual appearance as shown in FIG. 1B. In FIG. 1B, the device 100 has a predetermined colour, pattern or other visually distinctive property. Further, in some embodiments the device 100 as shown in FIG. 1B has a greater opacity in the first visual appearance than in the second visual appearance. As will be apparent, the re-application of sunscreen to the skin 104 and the device 100 reduces or eliminates exposure of the device 100 to ultraviolet radiation, in response to which the device 100 returns to the second visual appearance shown in FIG. 1A.

In other embodiments, the second visual appearance also has a visible colour, different from the colour of the first visual appearance. Preferably, the respective colours of the first and second visual appearance are contrasting (e.g. orange and purple). In further embodiments, the first visual appearance can be substantially colourless and transparent while the second visual appearance can have a predetermined colour and opacity.

The device 100 has various structural and material properties that permit the above-mentioned transitions between visual appearances not only to take place, but to take place at functionally appropriate times (e.g. when the sunscreen applied to the skin 104 adjacent to the device 100 has ceased to be effective at absorbing or reflective ultraviolet radiation). Those properties are discussed below in greater detail.

Figure 2:
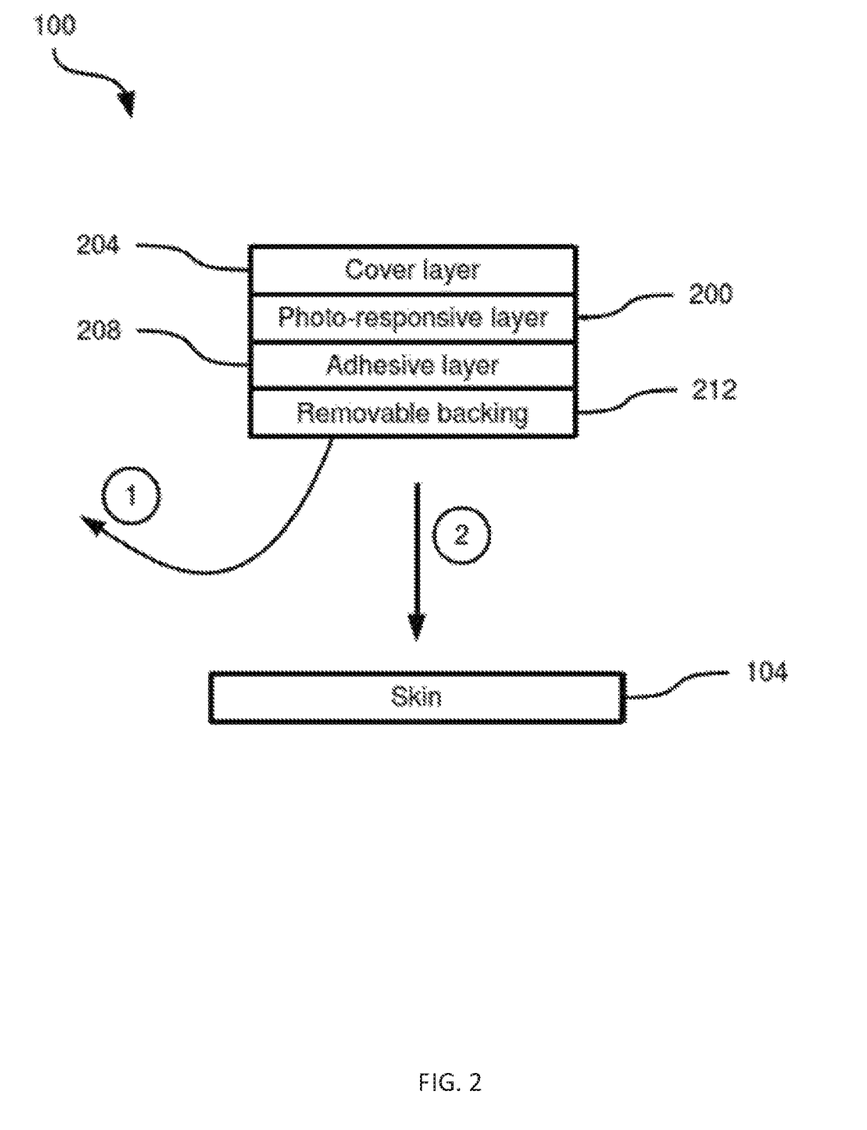

Turning to FIG. 2, a schematic cross-section of the device 100 according to certain embodiments is illustrated. As shown in FIG. 2, the device 100 includes the above-mentioned photo-responsive layer 200, which includes a photochromic material selected to provide the transitions between visual appearances described above. The device 100 also includes a skin-mimicking cover layer 204 (also referred to herein simply as the cover layer 204) covering a first side of the photo-responsive layer 200. The first side of the photo-responsive layer 200 that is covered by the cover layer 204 refers to the side of the photo-responsive layer 200 furthest from the skin 104 after application of the device 100 to the skin 104. The first layer may therefore also be referred to as the upper, or outer, layer of the device 100 (i.e. the layer furthest away from the skin 104 after the device 100 has been applied).

The composition and structure of the cover layer 204 will be discussed in greater detail below; in general, the composition and structure of the cover layer 204 simulate certain characteristics of the skin 104. For example, in some embodiments the cover layer 204 simulates the characteristics of the skin 104 that permit sunscreen to wear off. Thus, in some embodiments, the cover layer 204 permits sunscreen to wear away under the effects of abrasion, contact with water, and the like, at approximately the same rate as does the skin 104 under such effects.

The device 100 also includes an adhesive layer 208 configured to couple a second side of the photo-responsive layer 200 opposite the first side to a surface, such as the surface of the skin 104. In other words, the adhesive layer 208 forms the inner or lower surface of the device 100 when applied to the skin 104.

The adhesive layer 208 includes an adhesive coating applied to the lower side of the photo-responsive layer 200 or to the lower side of a layer connected between the photo-responsive layer 200 and the adhesive layer 208 (as will be seen below). Any suitable one of, or combination of, a variety of adhesives can be employed for the adhesive layer 208. In some embodiments, the adhesive layer 208 includes an acrylic-based adhesive for medical and/or surgical use, which is therefore suitable for removably binding to the skin 104. The adhesive layer 208 is preferably selected to be able to bind to the surface (e.g. the skin 104) in the presence of water (including freshwater, saltwater, sweat exuded from the skin 104, and the like). For example, in some embodiments the adhesive layer 208 includes medical-grade adhesives such as Pros-Aide™.

The device 100 also includes, in certain embodiments, a removable backing 212 affixed to the adhesive layer 208 before use of the device 100. In certain embodiments, a single sheet of removable backing 212 can support a plurality of devices 100. In other embodiments, a single piece of removable backing 212 is provided for each device 100. The removable backing 212 serves to prevent the inadvertent attachment of the adhesive layer 208 to surfaces other than the desired surface (e.g. the skin 104), as well as to prevent the adherence of debris to the adhesive layer 208 before use of the device 100.

A variety of materials can be employed to provide the removable backing 212, as will be apparent to those skilled in the art. In some embodiments, the removable backing 212 is made of a poly-coated kraft paper with silicone on the side facing the adhesive layer 208. In further embodiments, the removable backing 212 is made of antistatic-treated poly-coated kraft paper with silicone on the side facing the adhesive layer 208. The antistatic treatment may permit easier removal of the removable backing 212 prior to application of the device 100 to the skin 104.

In use, as will now be apparent to those skilled in the art, the removable backing 212 is removed (see encircled "1" in FIG. 2) shortly before application of the device 100 (see encircled "2" in FIG. 2) to the skin 104 or other target surface.

Various implementations are contemplated for the photo-responsive layer 200 and the cover layer 204, as will be discussed below. In each implementation, however, the photo-responsive layer 200 includes a photochromic material. Generally, photochromic materials are those which transition between different states in the presence of absence of light of various wavelengths, and therefore have different visual appearances (e.g. colours) in the presence or absence of the relevant type of light. The device 100, in embodiments in which detection and indication of ultraviolet radiation is provided, includes one or more photochromic materials in the photo-responsive layer 200 that transition between states in the presence or absence of ultraviolet light (i.e. between 10 nm and 400 nm in wavelength).

In some embodiments, the photo-responsive layer 200 includes a plurality of photochromic materials, each of which transitions at a different subset of the range of wavelengths defining ultraviolet light. In further embodiments, the photo-responsive layer 200 includes materials that are responsive (i.e. that undergo the above-mentioned transitions) not only to light, but also to temperature. Such materials are referred to as thermo-photochromic materials (also referred to as thermally reversible photochromic materials or photo-thermochromic materials). Examples of thermo-photochromic materials include materials in the class referred to as spiropyrans, an example of which is 1,3,3-trimethylindolino-6'-nitrobenzopyrylospiran. For example, in some embodiments, the photo-responsive layer 200 includes a thermo-photochromic material that transitions to a first visual appearance in the presence of light (e.g. UV light), but that returns to the second visual appearance only in the absence of such light and at a temperature at a certain threshold.

Preferably, the photochromic material or materials employed in the photo-responsive layer transition to the first visual appearance in the presence of radiation of a predetermined wavelength (e.g. ultraviolet light), and transition to the second visual appearance in the presence of a separate and distinct stimulus, such as radiation outside the range of wavelengths that the device 100 is configured to monitor and indicate for. That is, for a device configured to detect and indicate the presence (or absence) of ultraviolet radiation, the photochromic material or materials employed in the photo-responsive layer preferably transition to the first visual appearance upon exposure to radiation having wavelengths below 10 nm and above 400 nm (whether or not other types of radiation are present), and transition to the second visual appearance upon exposure to visible light having wavelengths above 400 nm (in the absence or reduced presence of ultraviolet light).

Examples of the photochromic materials employed in the photo-responsive layer 200 include materials in the class referred to as diarylethenes. An example of a diarylethene is 1,2-Bis(2,4-dimethyl-5-phenyl-3thienyl)-3,3,4,4,5,5-hexafluoro-1-cyclopentene, which undergoes a structural change in the presence of ultraviolet radiation (specifically, the molecule has an open-ring configuration in the absence of ultraviolet radiation, and a closed-ring configuration in the presence of ultraviolet radiation). The photochromic material can also be selected from various other classes of photochromic materials that will now be apparent to those skilled in the art as suitable for use in the device 100.

In some embodiments, the photo-responsive layer 200 may include thermo-photochromic materials, or a combination of thermo-photochromic materials and other photochromic materials. Thermo-photochromic materials may change colour at a different rate than other photochromic materials in the photo-responsive layer 200. Thus, a combination of thermo-photochromic materials and other photochromic materials may provide different stages of colour change, indicating different degrees of exposure to light radiation, on a device 100. In some embodiments, the thermo-photochromic materials and the other photochromic materials may be mixed in the photo-responsive layer 200 to provide a blended colour change. In other embodiments, the thermo-photochromic materials and the other photochromic materials may occupy different portions of the photo-responsive layer 200.

Figure 3A:
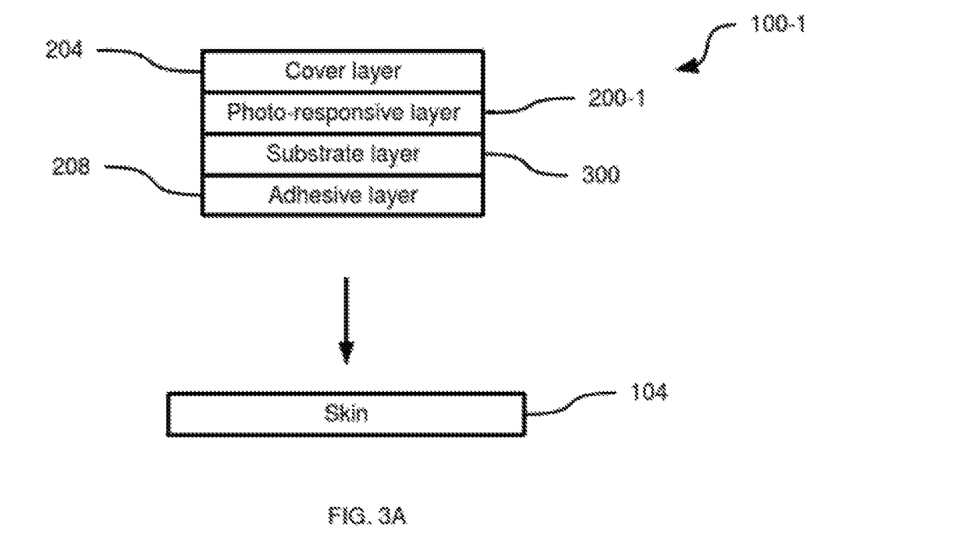
FIGS. 3A-3D, 4A-4B and 5 depict schematic cross-sections of the device of FIGS. 1A-1B, according to further non-limiting embodiments.
Figure 3B:
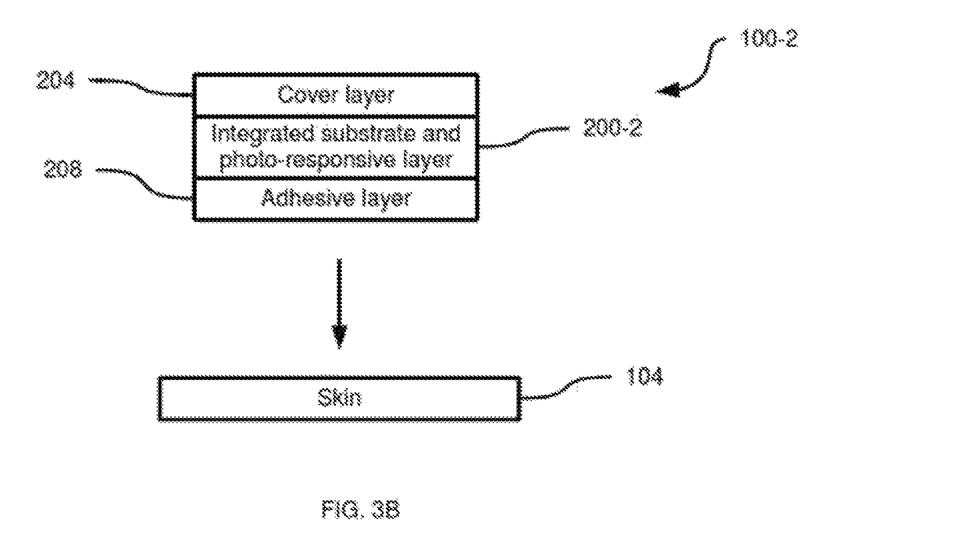

Turning now to FIGS. 3A and 3B, example implementations of the device 100 are discussed, in which a substrate material is included between the cover layer 204 and the adhesive layer 208 for supporting the photo-responsive layer 200. In these and subsequent examples, the removable backing 212 is omitted for simplicity of illustration, though it is contemplated that the removable backing 212 may be employed in any of the embodiments discussed below.

FIG. 3A illustrates an embodiment 100-1 of the device 100. The device 100-1 includes the cover layer 204 and the adhesive layer 208 as described above and as further detailed below. In addition, the device 100-1 includes a substrate layer 300 between the adhesive layer 208 and a photo-responsive layer 200-1. Herein, numerals appended to a reference numeral with a dash are employed to identify variations of the structure identified by the "base" numeral. Thus, references to the device 100 are intended as collective references to the device 100-1 and any other variations described herein. The same nomenclature is employed for components of the device 100.

The substrate layer 300 includes the above-mentioned substrate material, and provides a structural base on which the photo-responsive layer 200-1 and the cover layer 204 are supported, and on which the adhesive layer 208 is supported. In some embodiments, the substrate layer 300 and the adhesive layer 208 are manufactured together as an adhesive tape via the application of adhesive to a substrate membrane. For example, in some embodiments, during manufacture of the device 100-1 the photo-responsive layer 200-1 is applied to the substrate layer 300 as an ink. The application of the photo-responsive layer to the substrate layer 300 can be achieved by any suitable technology (e.g. printing, corona surface treatments and the like). In other embodiments, the photo-responsive layer 200-1 is applied to the substrate layer as a film (either in liquid or in solid state) containing an adhesive to bond to the substrate layer 300.

The substrate material forming the substrate layer 300 includes a material film which may be a polymer film; thus, the photochromic material and any carrier materials making up the photo-responsive layer 200-1 are applied to the upper surface of the material film. In some embodiments, in which the photo-responsive layer is printed onto the substrate layer 300, the material film is selected for suitability for the relevant printing technology, such as a solvent-based printing application. For example, the photochromic material can be dissolved (e.g. at about 3% by mass) in any suitable carrier material, such as FGN 4121. Thus, in certain embodiments the substrate material is a plastic film or membrane, comprising, for example, a polyester, polyethylene, polyurethane, polyamides, polylactates, polyvinyl-alcohols, -acetates, -acrylates and/or -pyrrolidones. In embodiments such as those discussed herein, in which the device 100 is applied to the skin 104 of a user, the substrate membrane is preferably breathable. In some embodiments, at least a portion of the substrate layer 300 is translucent or transparent to one or both of visible and ultraviolet radiation. In other embodiments, however, the substrate layer 300 is opaque and or reflective to one or both of visible and ultraviolet radiation.

Turning to FIG. 3B, another embodiment 100-2 of the device 100 is illustrated, including a photo-responsive layer 200-2 integrated with the above-mentioned substrate material. Thus, rather than being deposited or otherwise applied on the upper surface of the substrate layer 300, in the device 100-2, the photochromic material is physically or chemically integrated within the substrate material. As noted above in connection with FIG. 3A, the substrate material is a polymer suitable for forming into films in some embodiments. For example, the polymer can be a plastic or a blend of plastics (preferably breathable and/or translucent) such as polyester, polyethylene, polyurethane, polyamides, polylactates, polyvinyl-alcohols, -acetates, -acrylates and/or pyrrolidones. As will now be apparent, in the embodiment shown in FIG. 3B the substrate material is preferably translucent or transparent to ultraviolet radiation.

In some embodiments, the photochromic material is physically integrated with the substrate layer by cross-linking of the polymer. In other words, the integrated layer 200-2 is manufactured with the photochromic material and the substrate material being integrated during the formation of the integrated layer 200-2 rather than the substrate material being formed into a layer separately from the photochromic material (as in FIG. 3A).

Figure 3C:
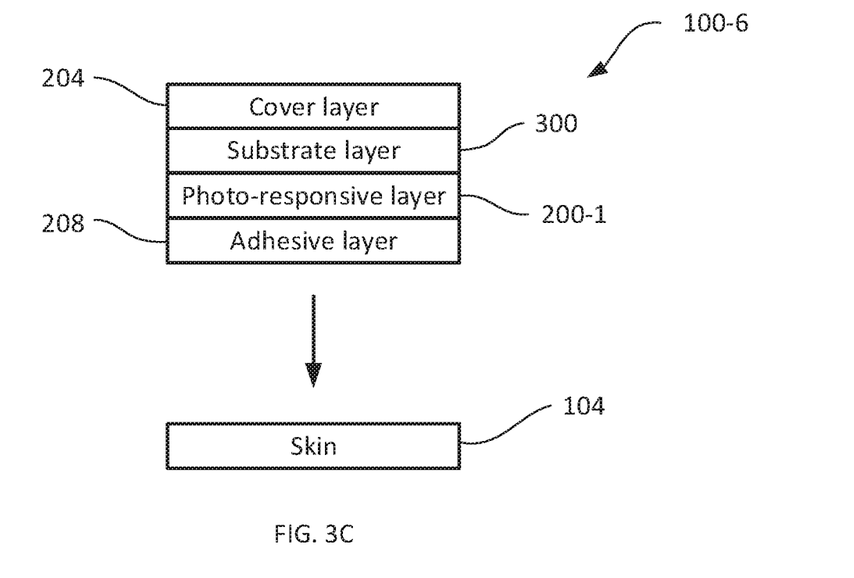

In an alternative embodiment shown in FIG. 3C, a device 100-6 includes a photo-responsive layer 200-1 applied to the bottom surface of a substrate layer 300 and on top of an adhesive layer 208. By applying the photo-responsive layer 200-1 to the bottom of substrate layer 300, cover layer 204 can be applied directly over the substrate layer 300. This may improve the durability of the cover layer 204 since the substrate layer 300 may be more readily adjusted to bond with the cover layer 204 more favourably. Additionally, having the photo-responsive layer 200-1 below the substrate layer 300 may further shield the photo-responsive layer 200-1 from environmental wear due to exposure to elements such as water, thereby reducing degradation of the photo-responsive layer 200-1.

Figure 3D:
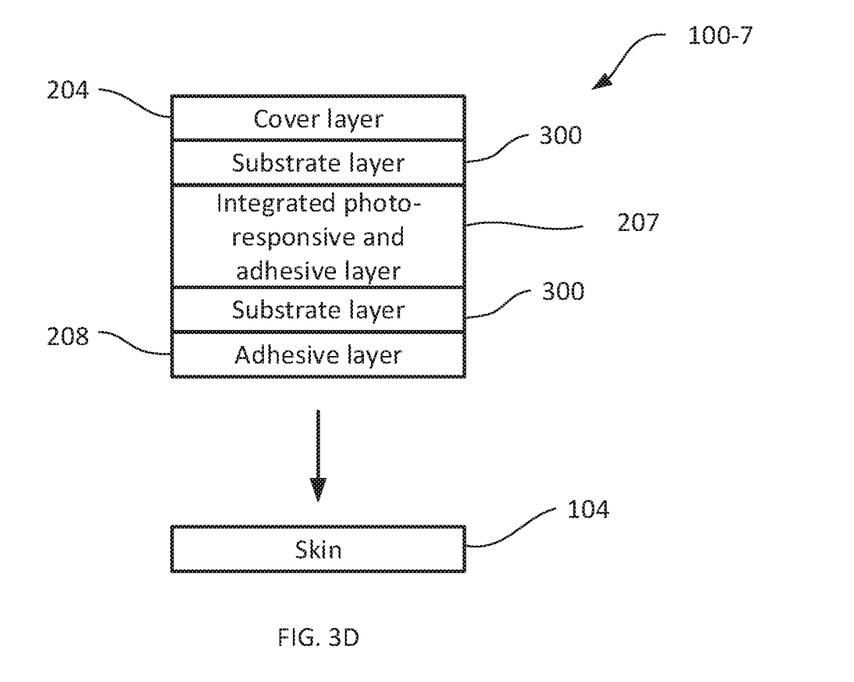

In an alternative embodiment shown in FIG. 3D, a device 100-7 includes an integrated photo-responsive and adhesive layer 207 (hereinafter integrated layer 207) sandwiched between two substrate layers 300. The two substrate layers 300 may further shield the integrated layer 207 from environmental wear and from other undesired interaction with the outside environment. Further, the two substrate layers 300 may inhibit direct interaction between cover layer 204 and the adhesive in integrated layer 207, which may provide for ease of production and resilience of the device. In some embodiments, the integrated layer 207 may be formed by dissolving a photochromic material at a concentration of up to about 8% by mass into an acrylic adhesive blend and applying the blend between two separate substrate layers 300. The wet thickness and concentration of the integrated layer 207 can be altered to give the desired colour intensity for the device 100-7. In some embodiments, the concentration of photochromic material may be about 4.2% by mass and the wet thickness of the integrated layer 207 may be about 2 millimetres. The two substrate layers 300 can be the same material or can be made of different compositions as described earlier above.

Figure 4A:
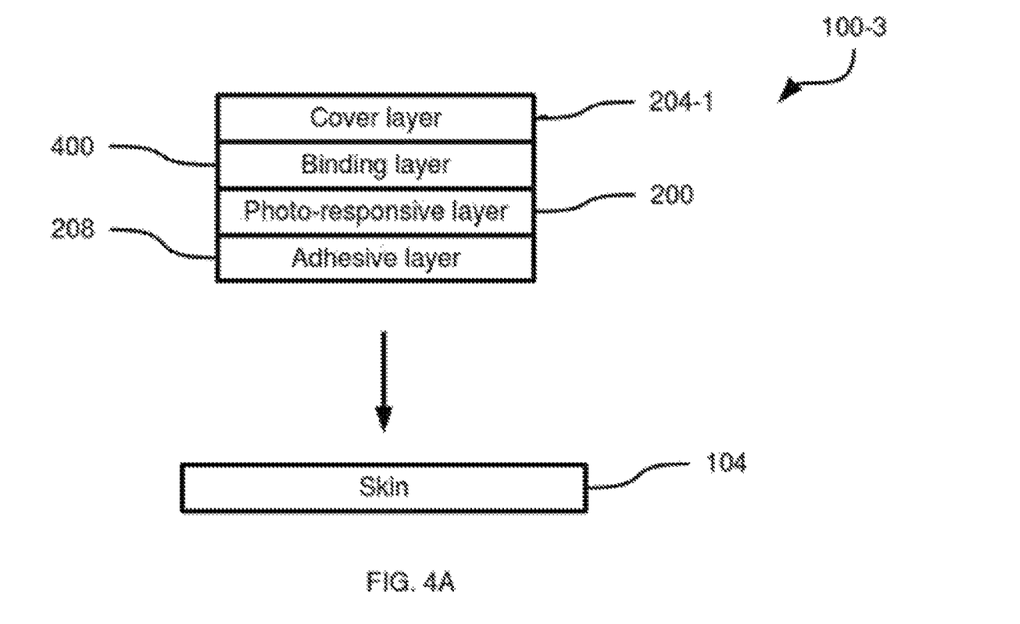
Figure 4B:
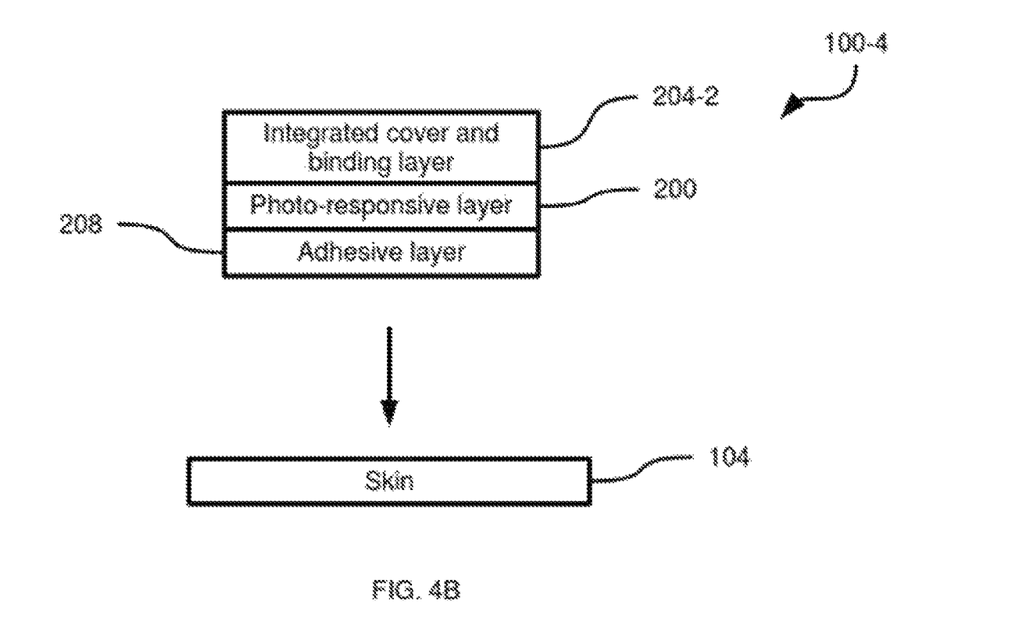

As noted earlier, the device 100 also includes the cover layer 204, whose composition and structure enable the device 100 to mimic certain properties of the skin 104. Referring now to FIGS. 4A and 4B, example implementations of the device 100 are discussed, in particular with regard to the implementation of the cover layer 204. Except as noted below, the example implementations of the cover layer 204 discussed below are applicable to any of the embodiments described above (including both of the devices 100-1 and 100-2 illustrated in FIGS. 2A-2B).

FIG. 4A illustrates a device 100-3 including the photo-responsive layer 200 (i.e. as noted above, either of the layers 200-1 and 200-2, or any other suitable variation thereof) and the adhesive layer 208. In addition, the device 100-3 includes a cover layer 204-1 connected to the photo-responsive layer 200 via a binding layer 400.

The cover layer 204-1 includes a polymer suitable for forming into a film. In some embodiments, the polymer is one of a polysaccharide and a polypeptide. In embodiments employing a polysaccharide polymer, polymers with cellulose backbones may be employed in the cover layer 204. More specifically, in some embodiments the polymer is chitosan, and the cover layer 204-1 is thus a film of chitosan, formed according to any suitable technique that will be apparent to those skilled in the art. The film of chitosan is degradable, and thus wears away in response to various environmental factors including abrasion, water exposure and the like. The rate at which the film degrades permits sunscreen to wear off device 100 at a rate that is similar to which sunscreen is worn off skin 104, and thus the cover layer 204-1 is said to mimic the skin 104.

The chitosan wet film comprises up to about 15% chitosan by mass. In certain embodiments, the chitosan wet film preferably comprises less than 10% chitosan by mass. The wet film can also include a solvent, such as acetic acid (e.g. up to about 10% by mass, and preferably below 5% by mass), to aid in the dissolution of the chitosan (permitting greater proportions of chitosan, e.g. up to about 15%, to be employed, thus increasing the mechanical strength of the resulting cover layer 204-1). The remainder of the wet film may be water, with the exception of certain optional additives, discussed below. The cover layer 204-1 is a dry film of chitosan and potential other additives, formed according to any suitable technique that will be apparent to those skilled in the art. The film would be deposited as a wet film during the manufacture of the device 100 and would be dried to form the final dry film which is cover layer 204. Drying of the wet film to create cover layer 204 is done through heat, air or any other techniques those skilled in the art would recognize. An example chitosan wet film includes 3% chitosan by mass and 5% glacial acetic acid by mass.

In another embodiment, the polymer in the cover layer 204-1 can be tapioca. In some embodiments, the cover layer 204-1 may be formed into a wet film comprising about 6% by mass tapioca, about 0.5% by mass chitosan, and about 0.25% by mass acetic acid. The acetic acid may assist with dissolution of chitosan. The remainder of the wet film may be water and certain optional additives, discussed below. The tapioca is a material having similar structure and skin-mimicking properties as chitosan, and has advantages in manufacturing and processing such as, for example, a difference in viscosity. Tapioca may also absorb no, or a minimal amount, of UV light radiation in the range of about 10 nm to about 400 nm, thereby allowing a greater proportion of light radiation to interact with photo-responsive layer 200. In other embodiments, other materials possessing qualities similar to tapioca may include guar gum, pectin and Iota-carrageenan. Those skilled in the art would understand that slight variations in concentrations and additives may be used.

In other embodiments, the polymer employed for the cover layer 204-1 is a polypeptide, such as gliadin (a component of gluten). The cover layer 204-1 is thus a film of gliadin formed according to any suitable technique that will be apparent to those skilled in the art. The film of gliadin is degradable and therefore simulates (i.e. mimics) the wear characteristics of the outer layer of the skin 104. The gliadin wet film comprises up to about 15% gliadin by mass. In certain embodiments, the gliadin wet film preferably comprises less than 10% gliadin by mass. The remainder of the wet film is water, with the exception of certain optional additives, discussed below.

In further embodiments, the cover layer 204-1 comprises a combination of a polysaccharide such as chitosan and a polypeptide such as gliadin. In such embodiments, the proportion of polymer in the cover layer 204-1 is up to about 20%, and is preferably below 10%, as in connection with the embodiments discussed above. However, the total proportion of polymer in the cover layer 204-1 is divided amongst the polysaccharide and the polypeptide. For example, in some embodiments the wet film comprises 5% chitosan and 5% gliadin. In other embodiments, one of the polymers accounts for a greater proportion of the cover layer 204-1 than the other. More generally, therefore, the wet film includes between about 0% and about 15% chitosan, with the remainder of the about 15% by mass being gliadin. The wet film also includes, in some embodiments, a solvent such as acetic acid to aid the dilution of the polymers therein. The remainder of the wet film is water, with the exception of certain optional additives, discussed below. Other combinations of polymers will also occur to those skilled in the art.

The cover layer 204-1, in addition to the polymers, water and (in some embodiments) solvent noted above, can include various additives. The additives include, in some embodiments, any one of or any suitable combination of thickening agents such as polyvinylpyrrolidone (e.g. about 1-5% by mass in the wet film). Other thickening agents include Gelmaker™ Style (e.g. about 0.5% by mass in the wet film) and glycerin (e.g. about 1-10% by mass in the wet film) for chitosan-based films, and triethanolamine (e.g. about 20% by mass for embodiments employing chitosan, or about 60% by mass for embodiments employing gliadin alone in the wet film) and xanthan gum (e.g. about 0.5-1.5% by mass in the wet film) for gliadin-based films. Thickening agents are employed to increase the viscosity of the polymer wet film. As will now be apparent, during manufacturing of the device 100, greater viscosities than those provided by combinations of the above-mentioned polymers with water alone may be more suitable to certain manufacturing techniques, such as continuous coating processes. For example, greater viscosities may allow the wet film to spread more evenly during manufacturing than in the absence of the above-mentioned thickening agents. The resulting cover layer 204-1 may therefore have an extended lifetime (i.e. may wear less easily).

The additives further include, in certain embodiments, pH-adjusting compounds. In particular, bases such as sodium hydroxide and triethanolamine are added to the film to achieve a target pH. The target pH is typically between about 5 and about 5.6. In some embodiments, the target pH is between 5.2 and 5.6. In some embodiments, the target pH is about 5.4, at which the distribution of the film is even, resulting in a cover layer 204-1 with a consistent thickness and therefore a predictable wear rate over the entire area of the device 100. For example, for a wet film comprising 1% chitosan and 1% acetic acid, about 0.005% sodium hydroxide and 2% triethanolamine were sufficient to balance the pH of the wet film at about 5.4. The above-identified ranges of pH have been found to be more effective than pH values between about 6 and about 7.

The additives further include, in certain embodiments, strength-enhancing materials that increase the mechanical strength of the resulting cover layer 204-1. Such additives include, for example, any suitable one of or any suitable combination of, triethanolamine (e.g. about 2% by mass in the wet film), sodium PCA (pyrrolidone carboxylic acid) (e.g. about 0.5% by mass in the wet film) and propylene glycol (e.g. about 5% by mass in the wet film). The above-mentioned additives increase the ability of the cover layer 204-1 to absorb water, and thus are employed to give the cover layer 204-1 a water content similar to that of the skin 104. In further embodiments, the additives also include a preservative, such as Ethylenediaminetetraacetic acid (EDTA) or its sodium salts (e.g. up to about 0.25% by mass in the wet film), Butylated hydroxytoluene (BHT) (e.g. up to about 0.05% by mass in the wet film) and propyl paraben (e.g. up to about 0.5% by mass in the wet film) or the like. Further additives that may be employed in the cover layer 204-1 include antioxidants such as ascorbic acid/ascorbates, propyl gallate, methylchloroisothiazolinone and/or anti-bacterial/anti-microbial agents such as benzoic acid, para-hydroxybenzoic acid (PHBA), sodium benzoate, hydroxybenzoate, citrus combo (e.g. up to about 1% by mass in the wet film) or other suitable anti-bacterial/anti-microbial agents.

In alternative embodiments, the cover layer 204-1 comprises a material suitable for forming into a film, the material including a protein extract and a polypeptide. In embodiments employing a protein extract, materials derived from collagen may be employed. In some embodiments, the material may include gelatin, and more particularly may include a dry film of gelatin and other additives as described below. The gelatin film can be deposited as a wet film during the manufacture of the device 100-3 and can be dried later to form the cover layer 204-1. Drying of the wet film to create cover layer 204-1 can be done through heat, air or any other techniques those skilled in the art would recognize. The film of gelatin is degradable, and thus wears away in response to various environmental factors including abrasion, water exposure and the like. The rate at which the film degrades permits sunscreen to wear off device 100 at a rate that is similar to which sunscreen is worn off skin 104, and thus the cover layer 204-1 is said to mimic the skin 104.

The gelatin wet film can comprise up to about 18% gelatin by mass. In certain embodiments, the gelatin film preferably comprises less than 6% gelatin by mass. However, wet films having different concentrations of gelatin are contemplated. Different concentrations of gelatin influences the viscosity of the film at temperatures below 30 degrees Celsius. The viscosity of the film can be modified to suit different manufacturing methods by adjusting the concentration of gelatin in the wet film. In some embodiments, the wet film can also include a polyol compound, such as glycerol (e.g. up to about 7% by mass, and preferably below about 4% by mass), to aid in the dissolution of the gelatin (altering the film to be more uniform, thus increasing the mechanical strength of the resulting cover layer 204-1). The wet film may also contain the polysaccharide chitin and/or its deacylated congener chitosan (up to about 1%) to increase the mechanical strength and antimicrobial properties of the resulting cover layer 204-1. The wet film may include an amount of acetic acid solvent (up to about 0.5% in the wet film) to help in the dissolution of chitin and chitosan. The remainder of the film may be water and certain optional additives, discussed below.

In some embodiments, the cover layer 204-1 can include various additives. The additives may include, in some embodiments, any one of or any suitable combination of thickening agents such as polyvinylpyrrolidone (e.g. about 1-5% by mass in the wet film). Thickening agents may be employed to increase the viscosity of the material solution. As will now be apparent, during manufacturing of the device 100-3, greater viscosities than those provided by combinations of the above-mentioned material with water alone may be more suitable to certain manufacturing techniques, such as continual coating processes. For example, greater viscosities may allow the film to spread more evenly during manufacturing than in the absence of the above-mentioned thickening agents. The resulting cover layer 204-1 may therefore have an extended lifetime (i.e. may wear less easily).

In further embodiments, the additives also include a preservative, such as Ethylenediaminetetraacetic acid (EDTA) or its sodium salts (e.g. up to about 0.25% by mass in the wet film), Butylated hydroxytoluene (BHT) (e.g. up to about 0.05% by mass in the wet film) and propyl paraben (e.g. up to about 0.5% by mass in the wet film) or the like. Further additives that may be employed in the cover layer 204-1 include antioxidants such as ascorbic acid/ascorbates, propyl gallate, methylchloroisothiazolinone and/or anti-bacterial/anti-microbial agents such as benzoic acid, para-hydroxybenzoic acid (PHBA), sodium benzoate, hydroxybenzoate, citrus combo (e.g. up to about 1% by mass in the wet film) or other suitable anti-bacterial/anti-microbial agents.

The cover layer 204-1 is translucent at least to ultraviolet radiation (in order to permit exposure of the underlying photo-responsive layer 200 to ultraviolet light when sunscreen has not been applied, or has worn off). Further, the cover layer 204-1 has a thickness selected to absorb at least a single application of sunscreen. In some embodiments, the cover layer 204-1 is provided with a greater thickness and/or a hardened film capable of absorbing two or more separate applications of sunscreen, permitting the device 100 to be re-used (i.e. permitting additional sunscreen to be applied) after the initial application of sunscreen has worn off. For example, the cover layer 204-1 can be deposited as a wet film having a thickness of between about 18 microns and about 220 microns.

As mentioned above, the device 100-3 also includes a binding layer 400 for binding the cover layer 204-1 to the photo-responsive layer 200. In some embodiments, the binding layer 400 includes an adhesive. The adhesive is translucent at least to ultraviolet radiation, and is preferably resistant to water and lotions such as sunscreen. For example, medical grade Pros-Aide™ adhesives are employed in some embodiments.

In some embodiments, the binding layer 400 includes a substrate material, such as a polymer film as described above in connection with the substrate layer 300. For example, in some embodiments the binding layer 400 includes a plastic membrane, such as polyethylene (e.g. low-density polyethylene) or polyurethane. A primer or adhesive as described above can be applied to one or both sides of the membrane, for binding the membrane to each of the photo-responsive layer 200 and the cover layer 204-1. Different primers or adhesives can be selected for each side of the membrane, for compatibility with the photo-responsive layer 200 and the cover layer 204-1, respectively.

Referring to FIG. 4B, a device 100-4 is illustrated according to a further embodiment. The device 100-4 includes an integrated cover and binding layer 204-2 rather than a separate binding layer as in FIG. 4A. The cover layer 204-2 includes a polymer film as described above, with the exception that the film also includes a binding material, including any one of, or combination of, an adhesive (e.g. Pros-Aide™ adhesives), and a surfactant or surface wetting agent. The surfactant changes the hydrophobicity of the underlying material (e.g. the photo-responsive layer 200 and the substrate layer 300, when employed). Making the underlying surface more hydrophilic enables the cover layer 204-2 to attach more favourably to the underlying surface. For example, the cover layer 204-2 includes (in addition to the polymers and optional additives as discussed above) example, Capstone™ FS-34 (e.g. about 0.5% by volume in the wet film).

Figure 5:
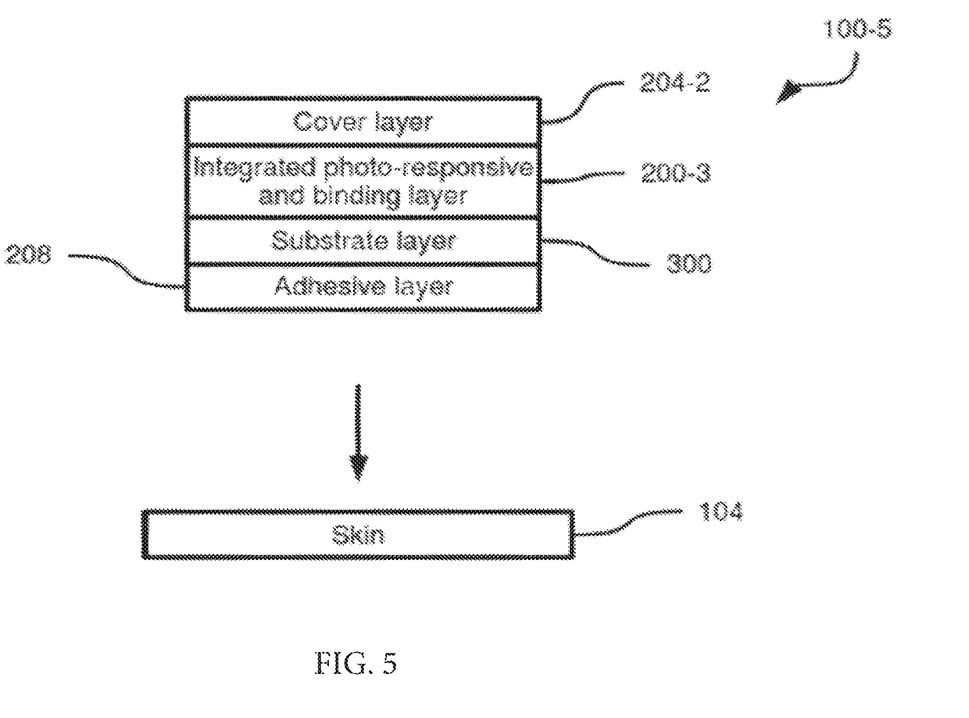

Turning to FIG. 5, in further embodiments, the above-mentioned binding material is integrated with the photo-responsive layer 200. In particular, a device 100-5 according to certain embodiments includes the cover layer 204-2 as described above, as well as the substrate layer 300 as discussed earlier, and an integrated photo-responsive and binding layer 200-3. The layer 200-3 includes a photochromic material as discussed earlier, in addition to any suitable combination of adhesives and surfactants as mentioned in connection with FIG. 4B.

In further embodiments, a device 100-5 according to certain embodiments includes the cover layer 204-2 as described above, as well as the substrate layer 300 as discussed earlier, and an integrated photo-responsive and binding layer 200-3. The layer 200-3 includes a photochromic material as discussed earlier, in addition to any suitable combination of adhesives but with another substrate layer located on the top side between layer 204-2 and 200-3 as mentioned in connection with FIG. 3D.

As will now be apparent, in some embodiments, the binding layer can simply be omitted. The cover layer 204 and the photo-responsive layer 200 can instead be formulated to adhere to each other, for example by the use of surface treatment methods (e.g. high frequency discharge). In further embodiments, combinations of the implementations of binding material shown in FIGS. 4A, 4B and 5 are employed. For example, in some embodiments the photo-responsive layer contains the photochromic material and an adhesive as discussed in connection with FIG. 5, and an additional layer (e.g. a plastic membrane) is included between the integrated photo-responsive and binding layer and the cover layer 204.

Figure 6:
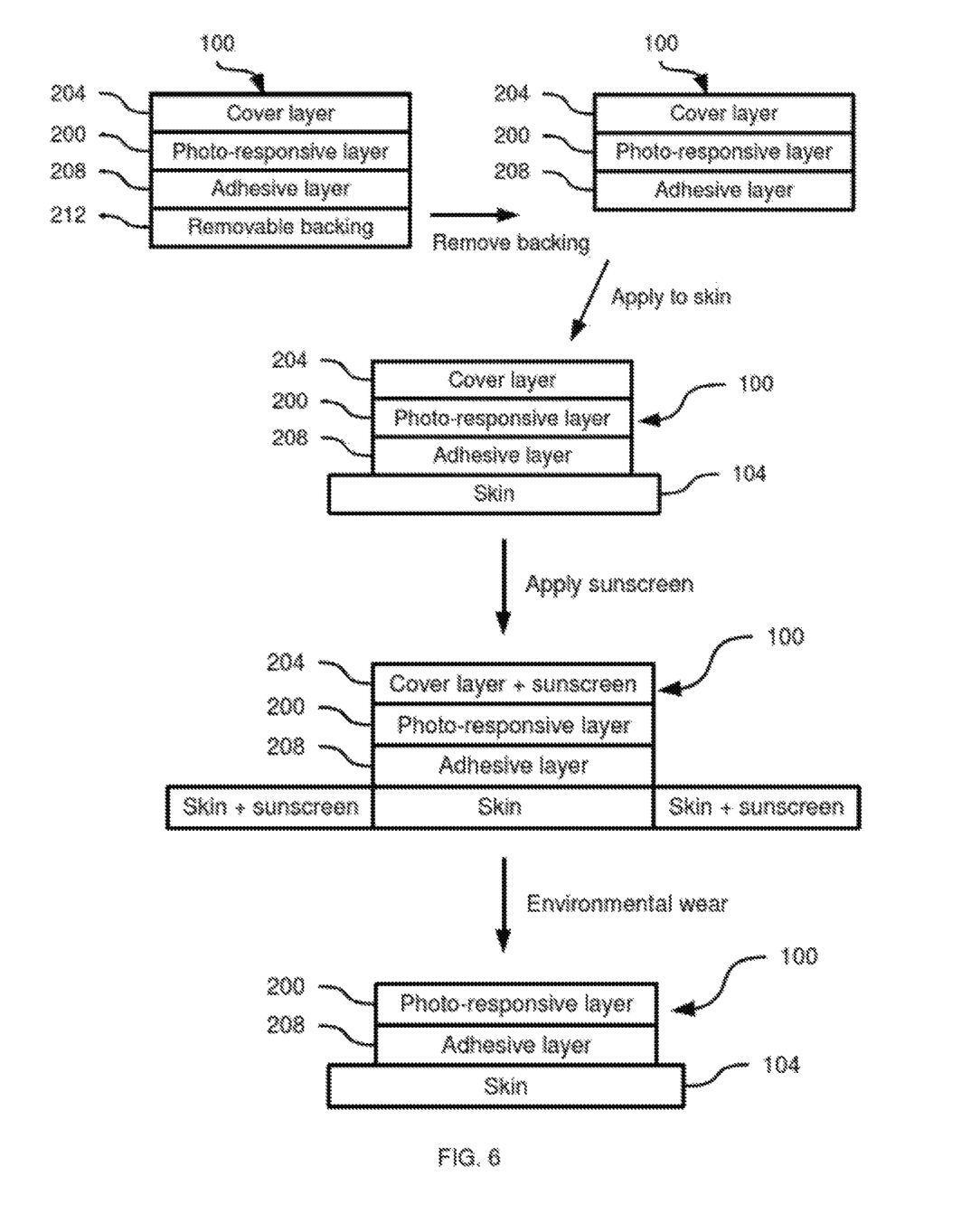
FIG. 6 depicts schematic cross-sections of the device of FIGS. 1A-1B in use, according to a non-limiting embodiment.

Referring now to FIG. 6, an example use case for a device 100 is illustrated. In particular, prior to use the removable backing 212 (if included) is removed. The device 100 is then applied to the surface for which detection and indication of light is desired. In the present example, the device 100 is applied to the skin 104 of a user, for detecting and indicating exposure of the skin to ultraviolet light. As will be apparent, immediately following application of the device 100 to the skin 104, the photo-responsive layer may be exposed to ultraviolet light (as no sunscreen has been applied). The photo-responsive layer may therefore transition to the first visual appearance as described above.

Following application of the device 100 to the skin 104, sunscreen is applied to the skin 104 and the device 100. The skin 104 and the cover layer 204 absorb the sunscreen, and are therefore protected from ultraviolet light. Following the application of sunscreen, the photo-responsive layer either transitions to the second visual appearance (if it was in the first visual appearance), or remains in the second visual appearance. However, following a certain degree of environmental wear, some of the sunscreen in the cover layer 204 may have worn away. In some instances, portions of the cover layer 204 (and the sunscreen carried therein) may have worn away, as has the outer layer of dead skin cells of the skin 104. Thus, the underlying (now outer) layer of the skin 104 may no longer be protected from ultraviolet light. As a result, the photo-responsive layer 200 transitions to the first visual appearance, indicating exposure to ultraviolet light.

In embodiments in which at least a portion of the cover layer 204 has remained in tact, sunscreen may be reapplied to the remaining (i.e. not worn away) portion of the cover layer 204. In some embodiments, after a subsequent application of sunscreen, the photo-responsive layer may return to its first visual appearance. In the example illustrated in FIG. 6, however, the device 100 is discarded, and a second device 100 may be applied, prior to the reapplication of sunscreen.

Figure 7:
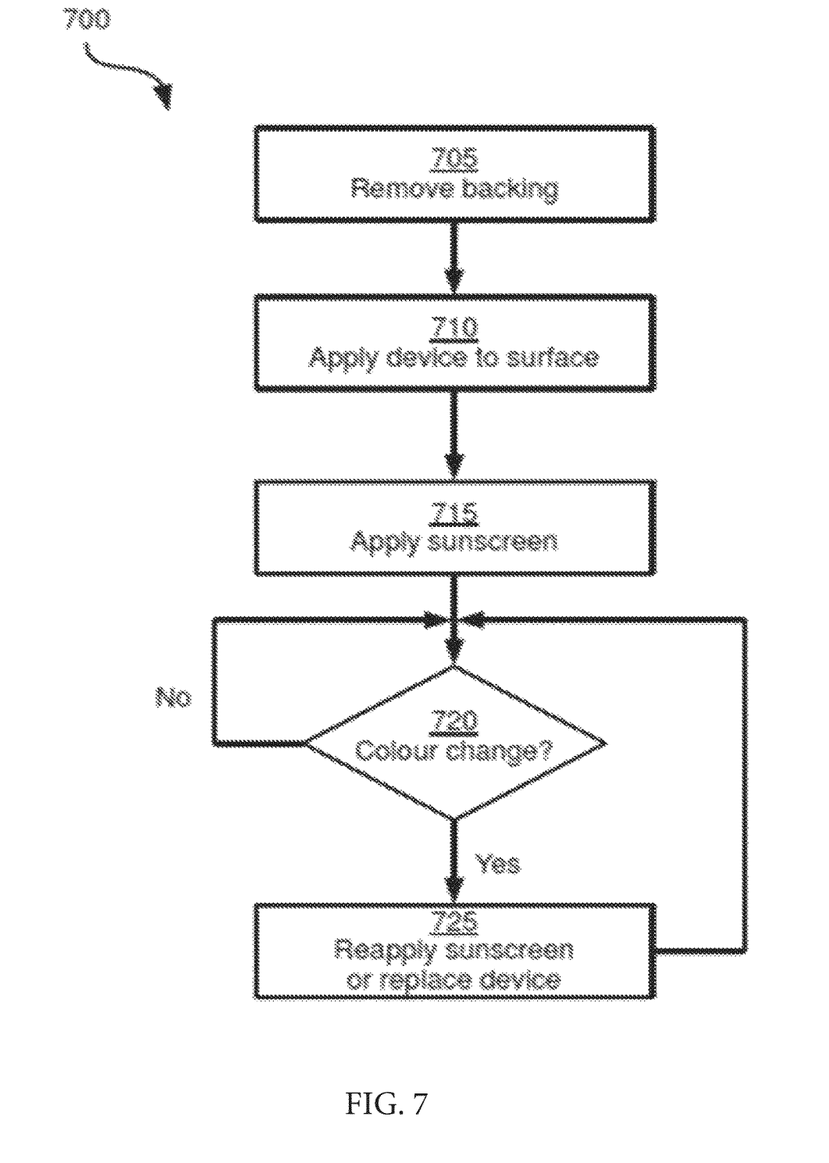
FIG. 7 depicts a method of using the device of FIGS. 1A-1B, according to a non-limiting embodiment.

From the above discussion, a method of using the device 100 will also now be apparent. In particular, referring to FIG. 7, a method 700 of using the device 100 is illustrated. At block 705, the backing 212 is removed, if present. At block 710, the device 100 is applied to the desired surface (e.g. the skin 104 of the user). At block 715, sunscreen is applied to the surface and the applied device 100. At block 720, a determination is made as to whether the device 100 has transitioned to the first visual appearance, indicating that the sunscreen is no longer effectively protecting the skin from ultraviolet light. When the determination is negative, the determination at block 720 is repeated. When the determination is affirmative, however, the performance of method 700 proceeds to block 725, at which sunscreen is reapplied (for devices with sufficiently thick cover layers 204 to allow reapplication) or the device is replaced.

Figure 8A:
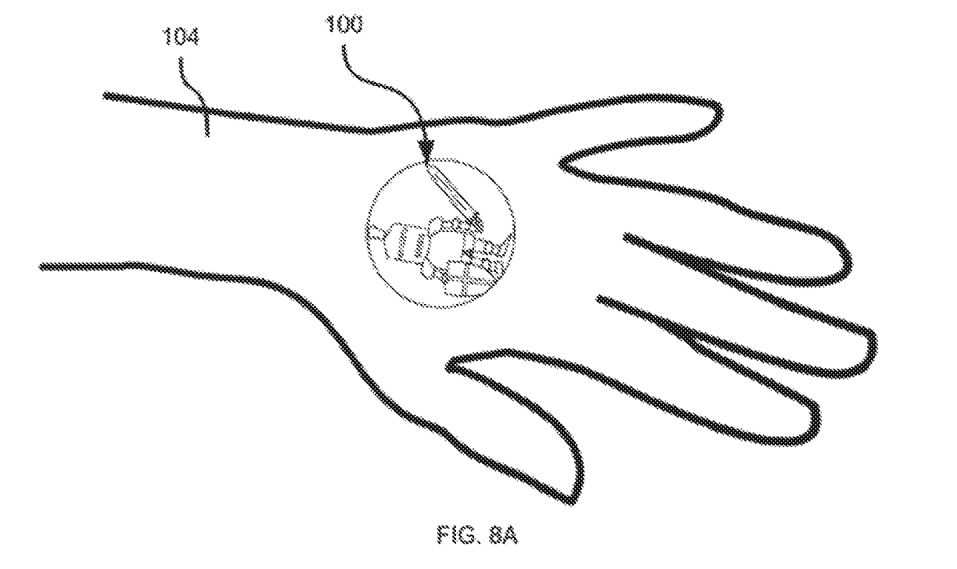
FIGS. 8A and 8B depict a device for detecting exposure to light in first and second visual appearances, according to another non-limiting embodiment.
Figure 8B:
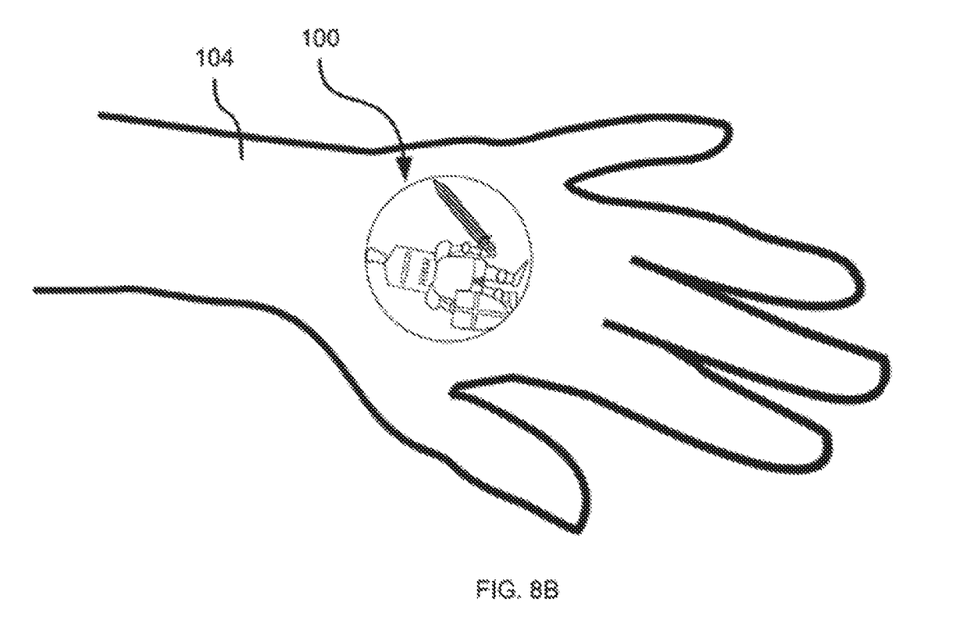

Variations in addition to those discussed are also contemplated. For example, in some embodiments the device 100 includes graphical indicia (e.g. printed on the substrate layer 300). As illustrated in FIGS. 8A and 8B, for example, the device 100 includes a graphic of a knight printed in non-photochromic ink. When the device 100 transitions from the second visual appearance (FIG. 8A) to the second visual appearance (FIG. 8B), a portion of the knight (the sword, in the present example) changes colour. In other words, the photo-responsive layer 200 includes photochromic material in only a portion of the area of the device 100, and the portion can coincide with a portion of a non-photochromic graphic on the device 100. Further, although the device 100 is illustrated as being circular in FIGS. 1A-1B and 8A-8B, the device 100 can be provided in a wide variety of other shapes (e.g. other polygons, letters, animals and the like).

The scope of the claims should not be limited by the embodiments set forth in the above examples, but should be given the broadest interpretation consistent with the description as a whole.

The invention claimed is:

1. A device for detecting exposure to light, comprising:
    a photo-responsive layer including a photochromic material;
    a skin-mimicking cover layer covering a first side of the photo-responsive layer, the cover layer to absorb an amount of sunscreen, wherein the cover layer includes a collagen-derived material to permit the amount of sunscreen to wear off the cover layer at a rate substantially the same as a rate at which the amount of sunscreen would wear off human skin;
    a first substrate layer of substrate material between the cover layer and the photo-responsive layer; and
    an adhesive layer configured to couple a second side of the photo-responsive layer opposite the first side to a surface.

2. The device of claim 1, the photo-responsive layer having a first visual appearance in the presence of light of a predetermined wavelength, and a second visual appearance in the absence of the light of the predetermined wavelength.

3. The device of claim 2, wherein the predetermined wavelength is between 10 nm and 400 nm.

4. The device of claim 2, wherein the first visual appearance has a first colour and the second visual appearance has a second colour.

5. The device of claim 2, wherein the first visual appearance has a first colour and the second visual appearance is colourless.

6. The device of claim 1, wherein the photo-responsive layer is integrated with an adhesive, and wherein the device further comprises:
    a second substrate layer of substrate material between the integrated photo-responsive and adhesive layer and the adhesive layer.

7. The device of claim 1, wherein the photochromic material comprises a thermo-photochromic material.

8. The device of claim 1, wherein the photo-responsive layer comprises the photochromic material and a thermo-photochromic material.

9. The device of claim 1, wherein the cover layer is degradable.

10. The device of claim 1, wherein the cover layer includes chitosan and tapioca.

11. The device of claim 1, wherein the cover layer is translucent.

12. The device of claim 1, further comprising a binding material configured to adhere the cover layer and the photo-responsive layer.

13. The device of claim 12, wherein the binding material is integrated with one of the cover layer and the photo-responsive layer.

14. The device of claim 1, wherein the cover layer further includes a polypeptide.

15. The device of claim 1, wherein the collagen-derived material includes gelatin.

16. The device of claim 15, wherein the cover layer includes a polyol compound.

17. The device of claim 16, wherein the cover layer includes a thickening agent.

18. The device of claim 1, further comprising a removable backing covering a side of the adhesive layer opposite the second side of the photo-responsive layer, the removable backing being removable prior to application of the device to the surface.

19. A device for detecting exposure to light, comprising:
    a photo-responsive layer including a photochromic material;
    a skin-mimicking cover layer covering a first side of the photo-responsive layer, the cover layer to absorb an amount of sunscreen, wherein the cover layer includes a collagen-derived material to permit the amount of sunscreen to wear off the cover layer at a rate substantially the same as a rate at which the amount of sunscreen would wear off human skin; and
    an adhesive layer configured to couple a second side of the photo-responsive layer opposite the first side to a surface;
    wherein the cover layer further comprises one or more of:
        gelatin and a polyol compound;
        a polypeptide; or
        chitosan and tapioca.

* * * * *